United States Patent
Rezach et al.

(10) Patent No.: US 11,957,391 B2
(45) Date of Patent: Apr. 16, 2024

(54) BONE SCREW HAVING AN OVERMOLD OF A SHANK

(71) Applicant: Warsaw Orthopedic, Inc., Warsaw, IN (US)

(72) Inventors: William A. Rezach, Covington, TN (US); Rodney R. Ballard, Lakeland, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 302 days.

(21) Appl. No.: 17/515,715

(22) Filed: Nov. 1, 2021

(65) Prior Publication Data

US 2023/0136340 A1    May 4, 2023

(51) Int. Cl.
*A61B 17/86*    (2006.01)
*A61B 17/70*    (2006.01)
*A61B 17/00*    (2006.01)

(52) U.S. Cl.
CPC ...... *A61B 17/8625* (2013.01); *A61B 17/7001* (2013.01); *A61B 17/866* (2013.01); *A61B 2017/00836* (2013.01); *A61B 2017/00955* (2013.01)

(58) Field of Classification Search
CPC .............. A61B 17/8625; A61B 17/866; A61B 17/8685
See application file for complete search history.

(56) References Cited

U.S. PATENT DOCUMENTS

| | | |
|---|---|---|
| 3,604,487 A | 9/1971 | Gilbert |
| 3,844,291 A | 10/1974 | Moen |
| 4,411,259 A | 10/1983 | Drummond |
| 5,020,519 A | 6/1991 | Hayes et al. |
| 5,113,685 A | 5/1992 | Asher et al. |

(Continued)

FOREIGN PATENT DOCUMENTS

| | | |
|---|---|---|
| DE | 4238339 C2 | 10/1994 |
| EP | 1725276 B1 | 4/2010 |

(Continued)

OTHER PUBLICATIONS

International Search Report and Written Opinion in Application No. PCT/IB2022/060465 dated Feb. 15, 2023.

(Continued)

*Primary Examiner* — Olivia C Chang
(74) *Attorney, Agent, or Firm* — FOX ROTHSCHILD LLP

(57) ABSTRACT

The present disclosure provides for a bone screw that may include a first portion extending from a first end to a second end in a longitudinal direction, for example. The first portion may have a head that defines the first end and a shank that defines the second end. Additionally, the first portion may include a metallic material and/or be formed of a metallic material, for example Titanium. The second portion may be mechanically coupled to the first portion and surround the shank, for example the second portion is screwed to the first portion or the second portion may be directly formed to the first portion by an overmold process. The second portion may have an exposed thread pattern and an exposed leading tip. Additionally, the second portion may include a thermoplastic material and/or be formed of a thermoplastic material such as PEEK.

11 Claims, 7 Drawing Sheets

(56) References Cited

U.S. PATENT DOCUMENTS

| | | |
|---|---|---|
| 5,207,678 A | 5/1993 | Harms et al. |
| 5,314,431 A | 5/1994 | Graziano |
| 5,330,472 A | 7/1994 | Metz-Stavenhagen |
| 5,364,397 A | 11/1994 | Hayes et al. |
| 5,389,099 A | 2/1995 | Hartmeister et al. |
| 5,443,467 A | 8/1995 | Biedermann et al. |
| 5,449,361 A | 9/1995 | Preissman |
| 5,458,608 A | 10/1995 | Wortrich |
| 5,466,243 A | 11/1995 | Schmieding et al. |
| 5,575,792 A | 11/1996 | Errico et al. |
| 5,609,593 A | 3/1997 | Errico et al. |
| 5,609,654 A | 3/1997 | Le et al. |
| 5,616,143 A | 4/1997 | Schlapfer et al. |
| 5,630,817 A | 5/1997 | Rokegem et al. |
| 5,643,263 A | 7/1997 | Simonson |
| 5,683,391 A | 11/1997 | Boyd |
| 5,720,751 A | 2/1998 | Jackson |
| 5,782,830 A | 7/1998 | Farris |
| 5,797,911 A | 8/1998 | Sherman et al. |
| 5,885,285 A | 3/1999 | Simonson |
| 5,885,286 A | 3/1999 | Sherman et al. |
| 5,899,901 A | 5/1999 | Middleton |
| 5,910,141 A | 6/1999 | Morrison et al. |
| 5,944,720 A | 8/1999 | Lipton |
| 5,947,967 A | 9/1999 | Barker |
| 5,964,760 A | 10/1999 | Richelsoph |
| 6,036,692 A | 3/2000 | Burel et al. |
| 6,042,582 A | 3/2000 | Ray |
| 6,063,088 A | 5/2000 | Winslow |
| 6,074,391 A | 6/2000 | Metz-Stavenhagen et al. |
| 6,110,172 A | 8/2000 | Jackson |
| 6,224,596 B1 | 5/2001 | Jackson |
| 6,280,442 B1 | 8/2001 | Barker et al. |
| 6,415,693 B1 | 7/2002 | Simon et al. |
| 6,440,133 B1 | 8/2002 | Beale et al. |
| 6,497,166 B1 | 12/2002 | Fleckenstein |
| 6,520,962 B1 | 2/2003 | Taylor et al. |
| 6,540,749 B2 | 4/2003 | Schafer et al. |
| 6,562,038 B1 | 5/2003 | Morrison |
| 6,565,566 B1 | 5/2003 | Wagner et al. |
| 6,572,618 B1 | 6/2003 | Morrison |
| 6,579,292 B2 | 6/2003 | Taylor |
| 6,641,586 B2 | 11/2003 | Varieur |
| 6,648,887 B2 | 11/2003 | Ashman |
| 6,685,705 B1 | 2/2004 | Taylor |
| 6,726,687 B2 | 4/2004 | Jackson |
| 6,730,089 B2 | 5/2004 | Jackson |
| 6,755,830 B2 | 6/2004 | Minfelde et al. |
| 6,786,903 B2 | 9/2004 | Lin |
| 6,857,343 B1 | 2/2005 | Easterbrooks et al. |
| 6,872,209 B2 | 3/2005 | Morrison |
| 6,918,911 B2 | 7/2005 | Biedermann et al. |
| 6,945,933 B2 | 9/2005 | Branch et al. |
| 7,066,939 B2 | 6/2006 | Taylor |
| 7,141,051 B2 | 11/2006 | Janowski et al. |
| 7,156,850 B2 | 1/2007 | Kim |
| 7,204,838 B2 | 4/2007 | Jackson |
| 7,211,086 B2 | 5/2007 | Biedermann et al. |
| 7,223,268 B2 | 5/2007 | Biedermann |
| 7,226,453 B2 | 6/2007 | Chao et al. |
| 7,378,144 B2 | 5/2008 | DeMeo et al. |
| 7,503,924 B2 | 3/2009 | Lee et al. |
| 7,530,992 B2 | 5/2009 | Biedermann et al. |
| 7,572,264 B2 | 8/2009 | Null et al. |
| 7,645,294 B2 | 1/2010 | Kalfas et al. |
| 7,717,939 B2 | 5/2010 | Ludwig et al. |
| 7,771,459 B2 | 8/2010 | von Oepen |
| 7,776,067 B2 | 8/2010 | Jackson |
| 7,846,167 B2 | 12/2010 | Garcia et al. |
| 7,896,902 B2 | 3/2011 | Jeon et al. |
| 7,947,047 B2 | 5/2011 | Arnal |
| 7,955,359 B2 | 6/2011 | Matthis et al. |
| 7,967,850 B2 | 6/2011 | Jackson |
| 7,972,364 B2 | 7/2011 | Biedermann et al. |
| 7,976,463 B2 | 7/2011 | Dewey et al. |
| 7,988,699 B2 | 8/2011 | Martz et al. |
| 8,025,680 B2 | 9/2011 | Hayes et al. |
| 8,034,086 B2 | 10/2011 | Iott et al. |
| 8,034,089 B2 | 10/2011 | Matthis et al. |
| 8,048,124 B2 | 11/2011 | Chin et al. |
| 8,075,590 B2 | 12/2011 | Janowski et al. |
| 8,097,025 B2 | 1/2012 | Hawkes et al. |
| 8,100,916 B2 | 1/2012 | Kumar et al. |
| 8,100,946 B2 | 1/2012 | Strausbaugh et al. |
| 8,123,784 B2 | 2/2012 | Biedermann et al. |
| 8,162,989 B2 | 4/2012 | Khalili |
| 8,167,910 B2 | 5/2012 | Nilsson |
| 8,172,876 B2 | 5/2012 | Janowski et al. |
| 8,197,518 B2 | 6/2012 | Hammill, Sr. et al. |
| 8,221,431 B2 | 7/2012 | Chenaux |
| 8,221,469 B2 | 7/2012 | Zehnder et al. |
| 8,221,472 B2 | 7/2012 | Peterson et al. |
| 8,226,690 B2 | 7/2012 | Altarac et al. |
| 8,231,635 B2 | 7/2012 | Sharifi-Mehr et al. |
| 8,262,670 B2 | 9/2012 | Laubert et al. |
| 8,267,969 B2 | 9/2012 | Altarac et al. |
| 8,298,265 B2 | 10/2012 | Purcell et al. |
| 8,298,275 B2 | 10/2012 | Rezach et al. |
| 8,328,850 B2 | 12/2012 | Bernard et al. |
| 8,343,165 B2 | 1/2013 | Berrevoets |
| 8,343,191 B2 | 1/2013 | Matthis et al. |
| 8,394,108 B2 | 3/2013 | McLean et al. |
| 8,459,155 B2 | 6/2013 | Canizares, Jr. et al. |
| 8,460,307 B2 | 6/2013 | Saidha et al. |
| 8,465,528 B2 | 6/2013 | Schumacher |
| 8,475,466 B2 | 7/2013 | Chenaux |
| 8,535,352 B2 | 9/2013 | Altarac et al. |
| 8,540,756 B2 | 9/2013 | Olsen et al. |
| 8,551,142 B2 | 10/2013 | Altarac et al. |
| 8,585,741 B2 | 11/2013 | Gabelberger et al. |
| 8,617,217 B2 | 12/2013 | Iott et al. |
| 8,637,064 B2 | 1/2014 | Lyu et al. |
| 8,679,162 B2 | 3/2014 | Strausbaugh et al. |
| 8,690,925 B2 | 4/2014 | Biedermann et al. |
| 8,691,136 B2 | 4/2014 | DeMeo et al. |
| 8,709,055 B2 | 4/2014 | Beyar et al. |
| 8,740,946 B2 | 6/2014 | Peterson et al. |
| 8,747,411 B2 | 6/2014 | Mitchell |
| 8,757,035 B2 | 6/2014 | Kerboul et al. |
| 8,763,499 B2 | 7/2014 | Dahners |
| 8,784,431 B1 | 7/2014 | Harder et al. |
| 8,784,455 B2 | 7/2014 | Matthis et al. |
| 8,806,973 B2 | 8/2014 | Ross et al. |
| 8,845,652 B2 | 9/2014 | Heinz |
| 8,870,927 B2 | 10/2014 | Matthis et al. |
| 8,882,775 B2 | 11/2014 | LaPosta et al. |
| 8,888,820 B2 | 11/2014 | Blain et al. |
| 8,888,827 B2 | 11/2014 | Harper et al. |
| 8,900,248 B2 | 12/2014 | Biyani |
| 8,900,280 B2 | 12/2014 | Paroth et al. |
| 8,911,478 B2 | 12/2014 | Jackson et al. |
| 8,920,470 B2 | 12/2014 | Ludwig et al. |
| 8,926,672 B2 | 1/2015 | Jackson et al. |
| 8,932,303 B2 | 1/2015 | Bouliane |
| 8,945,193 B2 | 2/2015 | Kirschman |
| 8,951,264 B2 | 2/2015 | Saidha et al. |
| 8,968,276 B2 | 3/2015 | Zemlok et al. |
| 8,968,374 B2 | 3/2015 | Hoof et al. |
| 8,986,349 B1 | 3/2015 | German et al. |
| 8,992,575 B1 | 3/2015 | Di Lauro et al. |
| 8,992,587 B2 | 3/2015 | Kirschman |
| 8,998,921 B2 | 4/2015 | Sharifi-Mehr et al. |
| 9,017,333 B2 | 4/2015 | Beale et al. |
| 9,055,943 B2 | 6/2015 | Zemlok et al. |
| 9,089,370 B2 | 7/2015 | Biedermann et al. |
| 9,089,371 B1 | 7/2015 | Faulhaber |
| 9,101,427 B2 | 8/2015 | Globerman et al. |
| 9,113,976 B2 | 8/2015 | Yevmenenko et al. |
| 9,131,962 B2 | 9/2015 | Cahill et al. |
| 9,138,279 B2 | 9/2015 | Laposta et al. |
| 9,144,437 B2 | 9/2015 | Matthis et al. |
| 9,144,444 B2 | 9/2015 | Jackson |
| 9,149,307 B2 | 10/2015 | Sandstrom et al. |
| 9,216,044 B2 | 12/2015 | Nuckley et al. |

(56) References Cited

U.S. PATENT DOCUMENTS

| | | |
|---|---|---|
| 9,259,254 B2 | 2/2016 | Iott et al. |
| 9,265,540 B2 | 2/2016 | Kirschman |
| 9,271,760 B2 | 3/2016 | Biedermann et al. |
| 9,295,500 B2 | 3/2016 | Marigowda |
| 9,314,274 B2 | 4/2016 | Amstutz et al. |
| 9,333,010 B2 | 5/2016 | Matthis et al. |
| 9,339,302 B2 | 5/2016 | Biedermann et al. |
| 9,358,046 B2 | 6/2016 | Nichols et al. |
| 9,387,025 B2 | 7/2016 | Santangelo et al. |
| 9,402,663 B2 | 8/2016 | Peterson et al. |
| 9,439,700 B2 | 9/2016 | Peterson et al. |
| 9,446,507 B2 | 9/2016 | Nino et al. |
| 9,498,254 B2 | 11/2016 | Spratt et al. |
| 9,526,549 B2 | 12/2016 | Beyar et al. |
| 9,526,553 B2 | 12/2016 | Bess et al. |
| 9,554,829 B2 | 1/2017 | Cahill et al. |
| 9,572,605 B2 | 2/2017 | Shipp |
| 9,597,135 B1 | 3/2017 | Miller et al. |
| 9,642,654 B2 | 5/2017 | Reimels et al. |
| 9,649,139 B2 | 5/2017 | Sharifi-Mehr et al. |
| 9,655,650 B2 | 5/2017 | Blain et al. |
| 9,655,652 B2 | 5/2017 | Biedermann et al. |
| RE46,431 E | 6/2017 | Jackson |
| 9,687,285 B2 | 6/2017 | Robinson |
| 9,724,149 B2 | 8/2017 | Trieu et al. |
| 9,743,957 B2 | 8/2017 | Jackson |
| 9,782,204 B2 | 10/2017 | Spratt et al. |
| 9,808,354 B2 | 11/2017 | Willis et al. |
| 9,820,740 B2 | 11/2017 | Zemlok et al. |
| 9,848,918 B2 | 12/2017 | Strausbaugh et al. |
| 9,855,076 B2 | 1/2018 | Nichols et al. |
| 9,855,087 B2 | 1/2018 | Divincenzo et al. |
| 9,918,747 B2 | 3/2018 | Spratt et al. |
| 9,936,979 B2 | 4/2018 | Peterson et al. |
| 9,949,731 B2 | 4/2018 | Erramilli et al. |
| 9,956,003 B2 | 5/2018 | Prevost |
| 9,968,378 B1 | 5/2018 | Johnson et al. |
| 9,968,384 B2 | 5/2018 | Fischer et al. |
| 9,974,586 B2 | 5/2018 | Globerman et al. |
| 9,980,754 B2 | 5/2018 | Harper et al. |
| 9,987,066 B2 | 6/2018 | Stad et al. |
| 10,004,541 B1 | 6/2018 | Jackson |
| 10,045,787 B2 | 8/2018 | Krebs et al. |
| 10,058,354 B2 | 8/2018 | Jackson et al. |
| 10,076,374 B2 | 9/2018 | Diduch et al. |
| 10,105,165 B2 | 10/2018 | Biedermann et al. |
| 10,117,684 B2 | 11/2018 | Saidha et al. |
| 10,154,867 B2 | 12/2018 | Globerman et al. |
| 10,160,105 B2 | 12/2018 | Nino et al. |
| 10,219,854 B2 | 3/2019 | Nino et al. |
| 10,226,282 B2 | 3/2019 | Spratt et al. |
| 10,245,077 B2 | 4/2019 | Jackson |
| 10,245,078 B2 | 4/2019 | Jackson |
| 10,265,102 B2 | 4/2019 | Jackson et al. |
| 10,274,021 B2 | 4/2019 | Victor et al. |
| 10,285,740 B2 | 5/2019 | May et al. |
| 10,349,986 B2 | 7/2019 | Wall et al. |
| 10,363,073 B2 | 7/2019 | Raina et al. |
| 10,368,917 B2 | 8/2019 | Mishra et al. |
| 10,390,967 B2 | 8/2019 | Livorsi et al. |
| 10,426,535 B2 | 10/2019 | Zander et al. |
| 10,433,883 B2 | 10/2019 | DiVincenzo et al. |
| 10,433,982 B2 | 10/2019 | Willis et al. |
| 10,448,978 B2 | 10/2019 | Wall et al. |
| 10,448,983 B2 | 10/2019 | Beyar et al. |
| 10,463,404 B2 | 11/2019 | Wall et al. |
| 10,470,805 B2 | 11/2019 | Biedermann et al. |
| 10,478,235 B2 | 11/2019 | Beale et al. |
| 10,568,668 B2 | 2/2020 | Biedermann et al. |
| 10,568,677 B2 | 2/2020 | DiVincenzo et al. |
| 10,575,877 B2 | 3/2020 | Harper et al. |
| 10,582,925 B2 | 3/2020 | Marks et al. |
| 10,603,078 B2 | 3/2020 | Simpson et al. |
| 10,603,081 B2 | 3/2020 | Harper et al. |
| 10,617,458 B2 | 4/2020 | Beyar et al. |
| 10,639,077 B2 | 5/2020 | Nichols et al. |
| 10,639,080 B2 | 5/2020 | Sharifi-Mehr et al. |
| 10,646,261 B2 | 5/2020 | Folger et al. |
| 10,653,457 B2 | 5/2020 | Erramilli et al. |
| 10,660,687 B2 | 5/2020 | Goodwin, Jr. et al. |
| 10,682,167 B2 | 6/2020 | Sandstrom et al. |
| 10,687,855 B2 | 6/2020 | Jackson et al. |
| 10,702,315 B2 | 7/2020 | Lindner |
| 10,702,316 B2 | 7/2020 | Heuer |
| 10,709,479 B2 | 7/2020 | Keyer et al. |
| 10,709,488 B2 | 7/2020 | Diduch et al. |
| 10,729,419 B2 | 8/2020 | Diduch et al. |
| 10,751,092 B2 | 8/2020 | Biedermann et al. |
| 10,751,095 B2 | 8/2020 | Jackson |
| 10,765,466 B2 | 9/2020 | Stad et al. |
| 10,779,872 B2 | 9/2020 | Smith et al. |
| 10,849,668 B2 | 12/2020 | Globerman et al. |
| 10,869,751 B2 | 12/2020 | Diduch et al. |
| 10,874,448 B2 | 12/2020 | Rees et al. |
| 11,191,582 B2 | 12/2021 | Tempco et al. |
| 11,224,470 B2 | 1/2022 | Tempco et al. |
| 11,317,957 B2 | 5/2022 | Preiss-Bloom et al. |
| 11,389,220 B2 | 7/2022 | Beyar et al. |
| 2002/0166421 A1 | 11/2002 | Bowerman |
| 2002/0169453 A1 | 11/2002 | Berger |
| 2003/0130659 A1 | 7/2003 | Haider |
| 2004/0176766 A1 | 9/2004 | Shluzas |
| 2005/0159750 A1 | 7/2005 | Doherty |
| 2005/0182410 A1 | 8/2005 | Jackson |
| 2005/0203519 A1 | 9/2005 | Harms et al. |
| 2005/0273101 A1 | 12/2005 | Schumacher |
| 2006/0041261 A1 | 2/2006 | Osypka |
| 2006/0052785 A1 | 3/2006 | Augostino et al. |
| 2006/0058794 A1 | 3/2006 | Jackson |
| 2006/0241593 A1 | 10/2006 | Sherman et al. |
| 2006/0241600 A1 | 10/2006 | Ensign et al. |
| 2007/0010816 A1 | 1/2007 | Wilkinson et al. |
| 2007/0122764 A1 | 5/2007 | Balfour et al. |
| 2007/0233071 A1 | 10/2007 | Dewey et al. |
| 2007/0260246 A1 | 11/2007 | Biedermann |
| 2007/0270839 A1 | 11/2007 | Jeon et al. |
| 2008/0015596 A1 | 1/2008 | Whipple |
| 2008/0041196 A1 | 2/2008 | Companioni et al. |
| 2008/0071274 A1 | 3/2008 | Ensign |
| 2008/0147126 A1 | 6/2008 | Tipirneni et al. |
| 2008/0147128 A1 | 6/2008 | Fritzinger |
| 2008/0154373 A1 | 6/2008 | Protopsaltis et al. |
| 2008/0200918 A1 | 8/2008 | Spitler et al. |
| 2008/0215099 A1 | 9/2008 | Balfour et al. |
| 2008/0269768 A1 | 10/2008 | Schwager et al. |
| 2009/0005787 A1 | 1/2009 | Crall et al. |
| 2009/0204155 A1 | 8/2009 | Aschmann |
| 2009/0264895 A1 | 10/2009 | Gasperut et al. |
| 2010/0010543 A1 | 1/2010 | Jackson |
| 2010/0063546 A1 | 3/2010 | Miller et al. |
| 2010/0249798 A1 | 9/2010 | Sournac et al. |
| 2010/0249846 A1 | 9/2010 | Simonson |
| 2011/0077693 A1 | 3/2011 | Yu |
| 2011/0093021 A1 | 4/2011 | Fanger et al. |
| 2011/0098755 A1 | 4/2011 | Jackson |
| 2011/0125196 A1 | 5/2011 | Quevedo et al. |
| 2011/0137320 A1 | 6/2011 | von Oepen |
| 2011/0160775 A1 | 6/2011 | Carls et al. |
| 2011/0257686 A1 | 10/2011 | Metcalf, Jr. et al. |
| 2011/0257689 A1* | 10/2011 | Fiechter ............ A61B 17/866 606/301 |
| 2011/0270321 A1 | 11/2011 | Prevost et al. |
| 2011/0270322 A1 | 11/2011 | Olsen et al. |
| 2011/0282398 A1 | 11/2011 | Overes et al. |
| 2011/0301650 A1 | 12/2011 | Johnson et al. |
| 2012/0046700 A1 | 2/2012 | Jackson et al. |
| 2012/0123481 A1 | 5/2012 | Lin |
| 2012/0197313 A1 | 8/2012 | Cowan |
| 2012/0203286 A1 | 8/2012 | Armstrong et al. |
| 2012/0203288 A1 | 8/2012 | Lange et al. |
| 2012/0215263 A1 | 8/2012 | Lee |
| 2012/0239091 A1 | 9/2012 | Biedermann et al. |
| 2012/0239095 A1 | 9/2012 | Barrall |
| 2012/0253398 A1 | 10/2012 | Metcalf et al. |

(56) References Cited

U.S. PATENT DOCUMENTS

| | | |
|---|---|---|
| 2012/0277798 A1 | 11/2012 | Benson et al. |
| 2012/0283787 A1 | 11/2012 | Yuan et al. |
| 2013/0072984 A1 | 3/2013 | Robinson |
| 2013/0072986 A1 | 3/2013 | Robinson |
| 2013/0096618 A1 | 4/2013 | Chandanson et al. |
| 2013/0261671 A1 | 10/2013 | Horvath |
| 2014/0018816 A1 | 1/2014 | Fenn et al. |
| 2014/0052190 A1 | 2/2014 | Biedermann et al. |
| 2014/0066945 A1 | 3/2014 | Humphreys et al. |
| 2014/0142639 A1 | 5/2014 | Vennard et al. |
| 2014/0172027 A1 | 6/2014 | Biedermann et al. |
| 2014/0214084 A1 | 7/2014 | Jackson et al. |
| 2014/0257411 A1 | 9/2014 | Rezach |
| 2014/0288567 A1 | 9/2014 | Kroll |
| 2014/0324062 A1 | 10/2014 | Heuer et al. |
| 2015/0039034 A1 | 2/2015 | Frankel et al. |
| 2015/0119942 A1 | 4/2015 | Jackson et al. |
| 2015/0201972 A1 | 7/2015 | Doubler et al. |
| 2015/0201987 A1 | 7/2015 | Lemoine et al. |
| 2015/0250521 A1 | 9/2015 | Poker et al. |
| 2015/0359575 A1 | 12/2015 | Pech et al. |
| 2015/0374417 A1 | 12/2015 | Petit et al. |
| 2016/0022341 A1 | 1/2016 | Agarwal |
| 2016/0278815 A1 | 9/2016 | Fitzpatrick |
| 2016/0317206 A1 | 11/2016 | Rezach et al. |
| 2017/0119537 A1 | 5/2017 | Tepper et al. |
| 2017/0209178 A1 | 7/2017 | Cahill et al. |
| 2017/0245898 A1 | 8/2017 | May et al. |
| 2018/0049777 A1 | 2/2018 | Rezach |
| 2018/0070941 A1 | 3/2018 | Zemlok et al. |
| 2018/0071000 A1 | 3/2018 | Pham et al. |
| 2018/0110548 A1 | 4/2018 | May et al. |
| 2018/0146990 A1 | 5/2018 | Manzanares et al. |
| 2018/0153600 A1 | 6/2018 | Koller et al. |
| 2018/0193062 A1 | 7/2018 | May |
| 2018/0193063 A1 | 7/2018 | May |
| 2018/0206890 A1 | 7/2018 | Rezach |
| 2018/0235684 A1 | 8/2018 | Hawkes et al. |
| 2018/0263665 A1 | 9/2018 | Yacoub et al. |
| 2018/0353224 A1 | 12/2018 | Kam et al. |
| 2019/0076170 A1 | 3/2019 | Lehman, Jr. et al. |
| 2019/0159820 A1 | 5/2019 | Geist et al. |
| 2019/0175193 A1 | 6/2019 | Fenn et al. |
| 2019/0183535 A1 | 6/2019 | May et al. |
| 2019/0209213 A1 | 7/2019 | Spratt et al. |
| 2019/0254729 A1 | 8/2019 | Rohlfing et al. |
| 2019/0254730 A1 | 8/2019 | Rohlfing et al. |
| 2019/0329388 A1 | 10/2019 | Erickson et al. |
| 2019/0336187 A1 | 11/2019 | Zander et al. |
| 2019/0357948 A1 | 11/2019 | Wall et al. |
| 2019/0374263 A1 | 12/2019 | Wall et al. |
| 2020/0030015 A1 | 1/2020 | Grizzard et al. |
| 2020/0038064 A1 | 2/2020 | Stoklund et al. |
| 2020/0078056 A1 | 3/2020 | Biedermann et al. |
| 2020/0100817 A1 | 4/2020 | DiVincenzo et al. |
| 2020/0100824 A1 | 4/2020 | DiVincenzo et al. |
| 2020/0113603 A1 | 4/2020 | Simpson et al. |
| 2020/0121397 A1 | 4/2020 | Elliott et al. |
| 2020/0121398 A1 | 4/2020 | Elliott et al. |
| 2020/0146725 A1* | 5/2020 | Geist ............... A61B 17/8695 |
| 2020/0205805 A1 | 7/2020 | Marks et al. |
| 2020/0205862 A1 | 7/2020 | Nichols et al. |
| 2020/0229849 A1 | 7/2020 | Biedermann et al. |
| 2020/0237412 A1 | 7/2020 | Erramilli et al. |
| 2020/0253644 A1 | 8/2020 | Biedermann |
| 2020/0323573 A1 | 10/2020 | Heino et al. |
| 2020/0340558 A1 | 10/2020 | Riemhofer et al. |
| 2020/0375638 A1 | 12/2020 | Avidano et al. |
| 2020/0390478 A1 | 12/2020 | Rodriguez et al. |
| 2020/0390486 A1 | 12/2020 | Rodriguez et al. |
| 2022/0087727 A1 | 3/2022 | Tempco et al. |
| 2022/0361932 A1 | 11/2022 | Beyar et al. |
| 2023/0136340 A1 | 5/2023 | Rezach et al. |
| 2023/0165613 A1 | 6/2023 | Miller et al. |

FOREIGN PATENT DOCUMENTS

| | | |
|---|---|---|
| EP | 3042621 B1 | 8/2017 |
| EP | 3678566 A1 | 7/2020 |
| EP | 3470097 B1 | 3/2021 |
| EP | 3799560 A1 | 4/2021 |
| EP | 3813701 A1 | 5/2021 |
| EP | 4115826 A1 | 1/2023 |
| FR | 2827757 A1 | 1/2003 |
| JP | 2001252283 A | 9/2001 |

OTHER PUBLICATIONS

CREO AMP® Stabilization System, Globus Medical, https://www.globusmedical.com/products/creo-amp/.

Globus Revere, <https://www.globusmedical.com/products/revere/>.

Globus Protex, https://www.globusmedical.com/products/protex/.

DePuy AcroMed, Monarch Spine System, https://www.youtube.com/watch?v=OpJj-T04Xuwg.

Pangea Degenerative Spine System Technique Guide, Synthes Spine, http://synthes.vo.llnwd.net/o16/LLNWMB8/INT%20Mobile/Synthes%20International/Product%20Support%20Material/legacy_Synthes_PDF/DSEM-SPN-0115-0250-2_LR.pdf.

Expedium® 5.5 Titanium Surgical Technique, Expedium Spine System, DePuy Synthes, http://synthes.vo.llnwd.net/o16/LLNWMB8/INT%20Mobile/Synthes%20International/Product%20Support%20Material/legacy_Synthes_PDF/105717.pdf.

Exactech (Vertiflex) Silverbolt, https://www.youtube.com/watch?v=RP9X72FOFLE.

\* cited by examiner

100

BONE SCREW HAVING AN OVERMOLD OF A SHANK

CROSS-REFERENCE TO RELATED APPLICATIONS

This application incorporates by reference the entire disclosure of U.S. Pat. No. 10,335,201, titled SPINAL IMPLANT SYSTEM AND METHODS OF USE, filed Jan. 25, 2017; U.S. Pat. No. 10,653,455 titled SPINAL IMPLANT SYSTEM AND METHODS OF USE filed Sep. 12, 2017; U.S. Pat. No. 6,790,209, titled ROD REDUCER INSTRUMENTS AND METHODS, filed Jul. 1, 2002; U.S. application Ser. No. 17/128,615, titled LOCKING CAP MODULE AND CONNECTOR and filed Dec. 12, 2020, U.S. application Ser. No. 17/167,734, titled LOCKING CAP MODULE AND CONNECTOR and filed Feb. 4, 2021, U.S. application Ser. No. 17/307,674 titled DORSAL ADJUSTING IMPLANT AND METHODS OF USE and filed Mar. 4, 2021, and U.S. application Ser. No. 17/318,279 titled TOP LOADING QUICK LOCK CONSTRUCT and filed Mar. 12, 2021.

FIELD

The present technology is generally related to bone screws for use in a medical context that may be formed of a first portion mechanically coupled to a second portion, for example. In some embodiments, the first portion may be referred to as a substrate and the second portion may be referred to as an overmold that may be formed directly on top of the substrate component. In some embodiments, the first portion (substrate) may be formed of a metallic material such as titanium and the second portion (overmold) may be formed of a plastic material such as Polyether ether ketone (PEEK).

BACKGROUND

A bone screw and/or pedicle screw may be implanted in a human patient for a variety of medical uses. At least one use involves the installation of a pedicle screw into a boney anatomy of a patient and the subsequent attachment of a receiver or connector to the pedicle screw for stabilization and/or fixation of the boney anatomy. Conventional bone screws and pedicle screws are formed of metallic materials, which are highly visible on an X-ray, and in some unwanted circumstances may block and/or otherwise hinder visibility of certain elements of patient anatomy.

SUMMARY

The techniques of this disclosure generally relate to a bone screw formed of a metallic first portion and a second portion formed of a plastic component directly on the first portion by an overmold or additive manufacturing process. In other embodiments, the first portion and the second portion may be threaded together or attached together by an adhesive, e.g., an epoxy.

In one aspect, the present disclosure provides for a bone screw. The bone screw may include a first portion extending from a first end to a second end in a longitudinal direction, for example. In various embodiments, the first portion may have a head that defines the first end and a shank that defines the second end, for example. In various embodiments, the first portion may include a metallic material and/or is formed of a metallic material, for example or may be of other materials including carbon fiber. In various embodiments, a second portion may be mechanically coupled to the first portion and surround the shank, for example. In various embodiments, the second portion may have an exposed thread pattern and an exposed leading tip, for example. In various embodiments, the second portion may include a thermoplastic material and/or be formed of a thermoplastic material, for example or may be of other materials including carbon fiber.

In another aspect, the disclosure provides for a bone screw product formed by an overmold process, for example. The bone screw product may include a substrate portion extending from a first end to a second end in a longitudinal direction, for example. In various embodiments, the substrate portion may have a head that defines the first end and a shank that defines the second end, for example. In various embodiments, the substrate portion may be formed of a metallic material, for example. In various embodiments, the bone screw product may include an overmold portion formed directly on top of the shank portion by an overmold process, for example. In various embodiments, the overmold portion may have an exposed thread pattern and an exposed leading tip, for example. In various embodiments, the overmold portion may include a thermoplastic material and/or be formed of a thermoplastic material. Additionally, in various embodiments, the overmold portion may surround the shank of the substrate portion and the head of the substrate portion may remain exposed.

In another aspect, the disclosure provides a spinal implant system. The spinal implant system may include a bone screw, for example. In various embodiments, the bone screw may include a first portion extending from a first end to a second end in a longitudinal direction, the first portion may have a head that defines the first end and a shank that defines the second end, for example. In various embodiments, the first portion may include a metallic material and/or be formed of a metallic material. In various embodiments, the second portion may be mechanically coupled to the first portion and surrounding the shank, for example. In various embodiments, the second portion may include an exposed thread pattern and an exposed leading tip, for example. In various embodiments, the second portion may include a thermoplastic material and/or be formed of a thermoplastic material, for example. The spinal system may further include a receiver having a rod receiving passageway extending through a first sidewall and through a second sidewall of the receiver, for example. In various embodiments, the receiver may have a threaded passageway configured to receive a set screw for securing the rod within the rod receiving passageway, for example. Additionally, the receiver may further include a base portion and at least one locking ring, for example. In various embodiments, in a coupled position, the head portion of the bone screw is securely coupled to the receiver via the base portion and the at least one locking ring.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
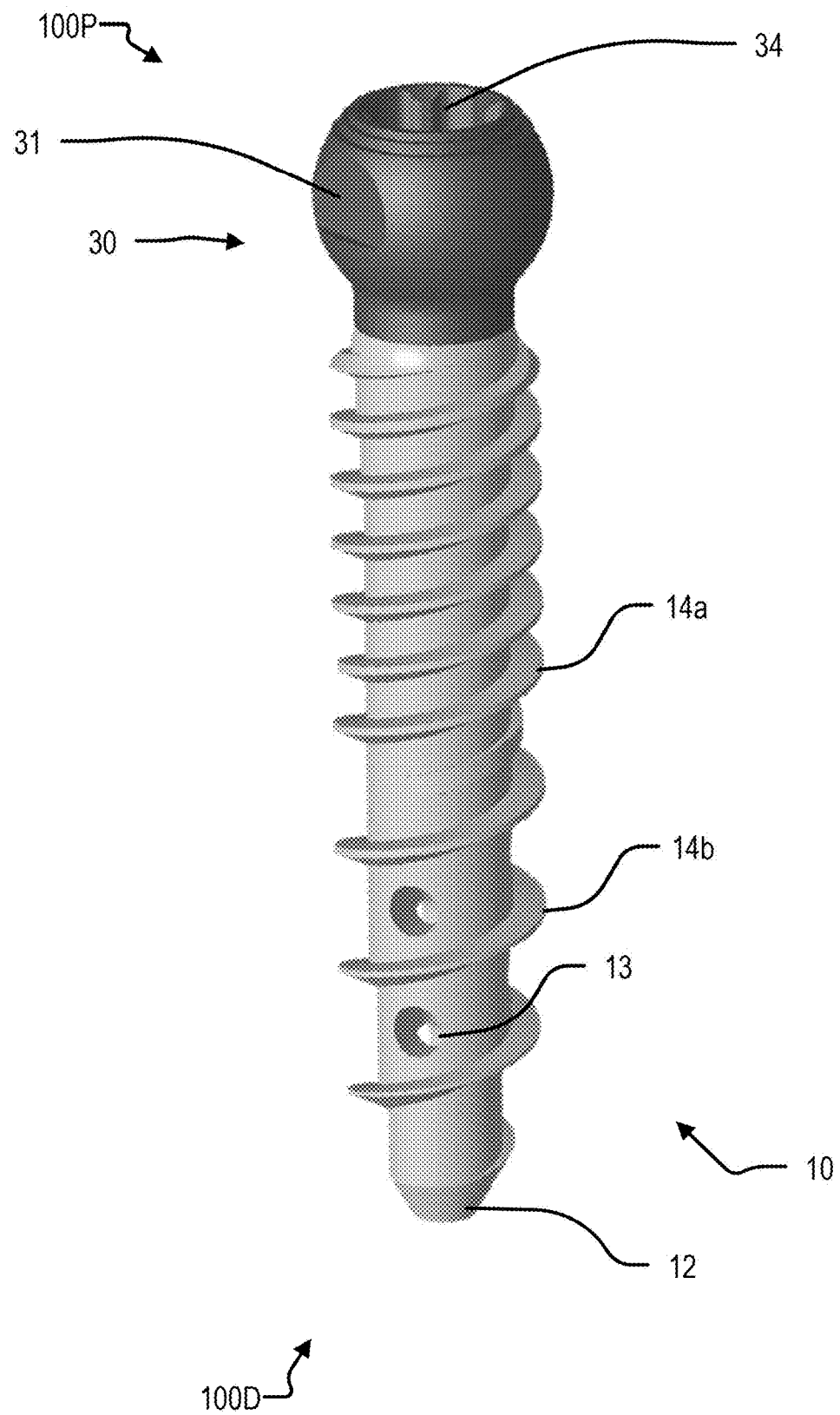
FIG. 1 is a front view of a bone screw.

Embodiments of the present disclosure relate generally, for example, to spinal stabilization systems, and more particularly, to bone screws having a metallic head and shank portion and a non-metallic overmold. In some embodiments, the head and shank may be formed of titanium and the overmold may be formed of PEEK. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Referring to FIGS. 1-4 generally, various bone screw embodiments and implant systems are disclosed. The components of bone screw 100 can be fabricated from biologically acceptable materials suitable for medical applications, including metals, synthetic polymers, ceramics and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Figure 2:
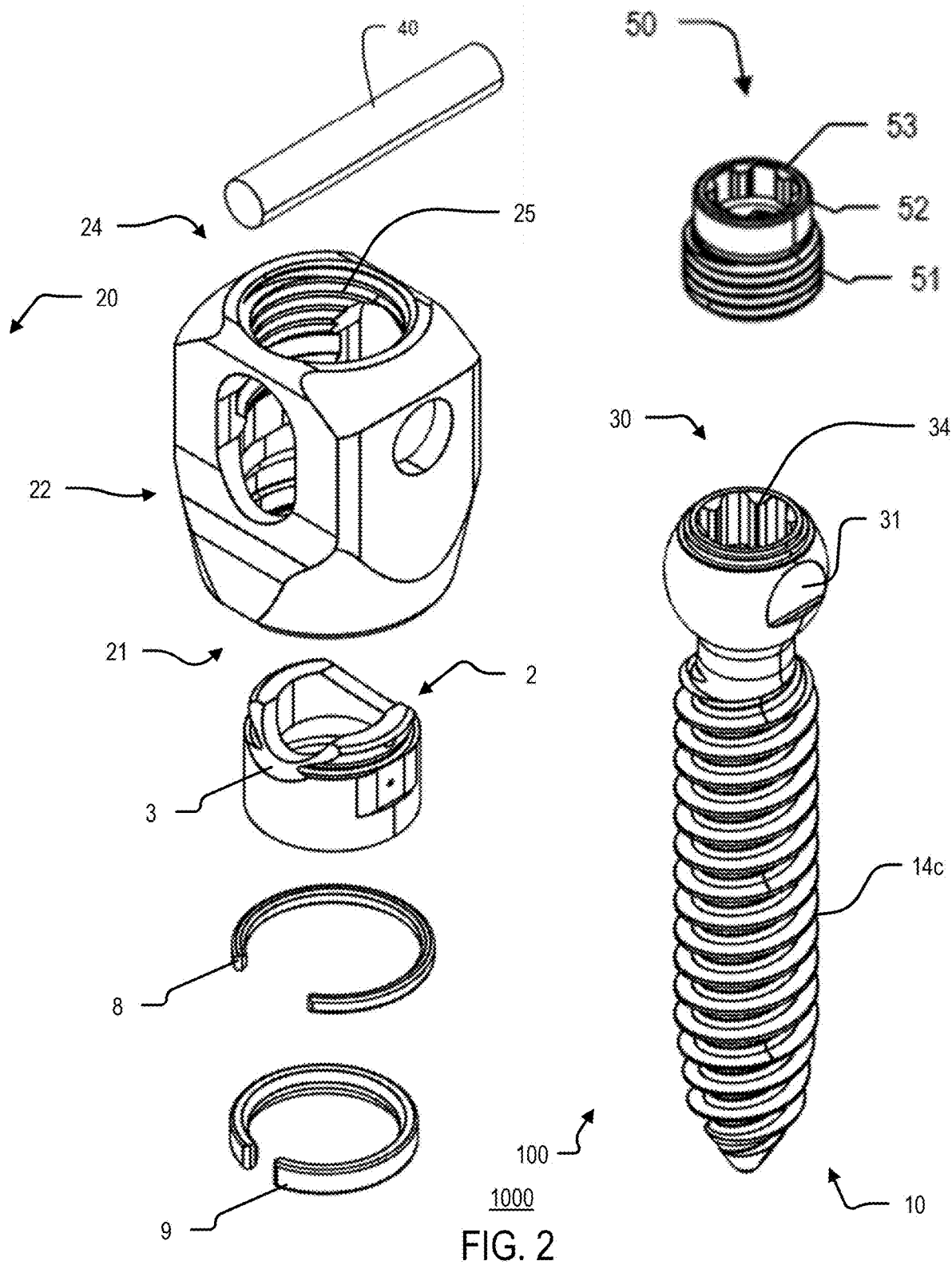
FIG. 2 is an exploded parts view of a receiver and a bone screw for attaching to the receiver.

Generally, FIGS. 1-4 illustrate various views and embodiments of a bone screw 100 and example implant systems 1000. FIG. 1 is a front view of a bone screw 100 and FIG. 2 is an exploded parts view of a receiver 20 and a bone screw 100 for attaching to the receiver 20. In the example embodiment, bone screw 100 may extend in a longitudinal direction from a proximal end 100P to a distal end 100D, for example. The proximal end 100P may include a first portion 30 comprising a head 31 having a drive interface 34, for example. The distal end 100D and medial portion may comprise a second portion 10, for example. The second portion 10 may be securely connected to the first portion 30 as will be explained in detail below.

In various embodiments, the first portion 30 may comprise a metallic material, be formed substantially of a metallic material, and/or be formed purely of a metallic material, e.g., titanium, titanium alloys, etc. However, it shall be understood that other biocompatible materials having similar material properties may also be used. In various embodiments, the second portion 10 may comprise a thermoplastic material, be formed substantially of a thermoplastic material, and/or be formed purely of a thermoplastic material, e.g., PEEK and PEEK composites. However, it shall be understood that other biocompatible materials having similar material properties may also be used.

Second portion 10 may include at least one thread pattern, for example first thread pattern 14a and second thread pattern 14b. In the example embodiment of FIG. 1, first thread pattern 14a has a different thread pitch than second thread pattern 14b, however other embodiments may include a continuous symmetrical thread pattern 14c (see FIG. 2). Additionally, second portion 10 may include a tip 12. Tip 12 may be a self-taping tip, a blunt tip, a pointed tip, a chisel tip, etc. In at least one embodiment, tip 12 is formed of a metallic material and the remaining part of second portion 10 is formed of a non-metallic material, e.g., any of those materials explained previously. In another embodiment, tip 12 is coated with a metallic material. In the example embodiment of FIG. 1, bone screw 100 is a fenestrated type screw having two openings 13 on a first side of bone screw 100 and another two openings 13 on a second side of bone screw 100 (not visible) which may be used in conjunction with Fenestrated Screw Cement, such as that sold by Medtronic under the brand name HV-R™ or a Bone Cement such as that sold by Medtronic under the brand name Kyphon™ Xpede™, for example. However, other embodiments may be formed with more or less openings 13 and/or as other types of bone screws 100, e.g., solid (see FIG. 2), cannulated, hybrid, self-taping, self-drilling, etc.

FIG. 2 illustrates an embodiment of bone screw 100 for use in conjunction with an implant receiver 20, for example.

Implant receiver 20 may include a threaded passageway 24 for rotatably supporting and receiving set screw 50, for example. Threaded passageway 24 may extend in the vertical direction and define a vertical axis of which set screw 50 may move upward and downward in upon rotation of set screw 50. Additionally, implant receiver 20 may include a passageway 22 for receiving rod 40, for example. Passageway 22 may extend in the horizontal direction and define a horizontal axis which rod 40 may be coaxially aligned with, for example. In the example embodiment, passageway 22 may be shaped like an oval when viewed in a side perspective view. In other embodiments, passageway 22 may be shaped like a circle, or a square or include an open top end, for example. In various embodiments, passageway 22 may have a size and shape generally corresponding to a size and shape of rod 40, for example. In various embodiments, a side view cross section of rod 40 may have an oval like shape generally corresponding to a size and shape of passageway 22 and/or any other shape corresponding to passageway 22, for example. In various embodiments, the rod may be formed of a non-metallic material, for example, PEEK or Carbon Fiber.

In the example illustrations, it is shown that set screw 50 may have an exterior thread pattern 51 having a timing and/or pitch including a size and shape generally corresponding to the timing and or pitch of threads 25 of threaded passageway 24 for example. Additionally, set screw 50 may include a breakoff portion 52 and a drive end 53 for coupling to a driver (not illustrated) to rotate set screw 50, for example. Drive end 53 may take any shape, for example a hexalobular shape, a hexaganol shape, a torx shape, etc. In operation, an end user may secure rod 40 within passageway 22 of implant receiver 20 and securely tighten set screw 50 by rotating set screw 50 at drive end 53 such that set screw 50 advances downward and secures rod 40 against the lower walls of passageway 22, for example.

In the example illustration, it is shown that implant receiver 20 may include a base portion 21 having a lower cavity configured to securely couple to bone screw 100 and support a crown 2 in a position above the head portion 31 of bone screw 100, for example. Crown 2 may include curved support surfaces 3 having a size and shape corresponding to a lower portion of the curved surface of rod 40, for example. Accordingly, crown 2 may support rod 40 from beneath rod 40 by directly contacting an underside of rod 40. Spinal implant system 1000 may further include an upper ring 8 and a lower ring 9. Upper and lower rings 8, 9 may be C-shaped and configured to securely couple head portion 31 of bone screw 100 within lower cavity of base portion 21, for example. Additional examples of how implant receiver 20 may securely connect to a bone screw 100 via an internal cavity of base portion 21 are also disclosed in detail in each of U.S. Pat. No. 10,335,201, titled Spinal Implant System and Methods of Use; and U.S. Pat. No. 10,653,455 titled Spinal Implant System and Methods of Use; U.S. application Ser. No. 17/167,258, titled Instrument for locking Orthopedic Screws, which are all incorporated herein by reference in their entireties.

In practice, a surgeon may initially couple the implant receiver 20 to bone screw 100 by pushing implant receiver 20 down against the bone screw 100 by, e.g., an instrument for locking orthopedic screws. For example, a surgical instrument may push implant receiver 20 down such that the upper and lower rings 8, 9 are seated around the head portion 31 of bone screw 100 and nested within and retained by corresponding cavities of base portion 21, for example. In seating upper and lower rings 8, 9 in corresponding cavities the head portion 31 of bone screw 100 experiences a mechanical stress. As explained previously, the first portion 30 of bone screw 100 may be formed of a metallic material. At least one advantage of this material choice is that the metallic first portion 30 is durable enough to sustain the wear and tear associated with coupling receiver 20 to the head portion 31 of bone screw 100. For example, the head portion 31 can sustain the reduction of receiver 20 and sustain the forces of the upper and/or lower rings 8, 9 as they compress the side surfaces of head portion 31 thereby pinning the upper portion 30 of bone screw 100 in the lower cavity 21 of receiver 20. Another advantage of this material choice is that metallic first portion 30 is also durable enough to withstand intra-operative correction forces.

Figure 3:
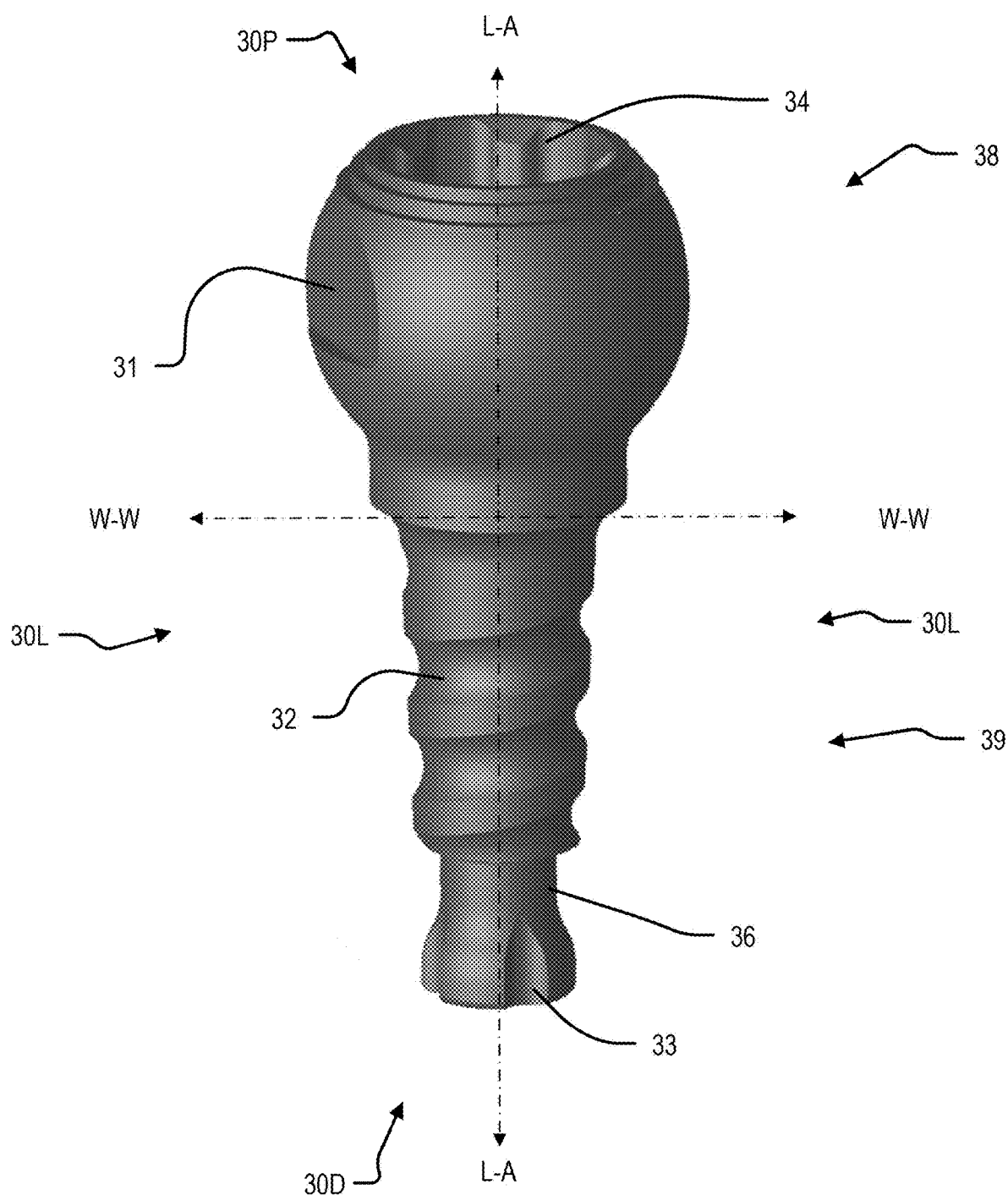
FIG. 3 is a front view of a head portion and shank portion of a bone screw.

FIG. 3 is a front view of a first portion 30 of a bone screw 100 comprising an upper portion 38 including the head portion 31 and a lower shank portion 39. First portion 30 may be formed as a single unitary component from stock material by a machining process, a casting process, or a molding process, for example. In the example embodiment, first portion 30 may extend in a longitudinal direction along axis L-A from a proximal end 30P to a distal end 30D and extend in a widthwise direction from a first lateral side 30L to a second lateral side 30L along axis W-W, for example. In various embodiments, the shank portion 39 may include various contours and textured surfaces such as indentations, outdents, diamond tread, etc. In the example embodiment, shank portion 39 includes a helical thread pattern 32 traversing the outside surface of shank portion 39 from head portion 31 to a necked down portion 36, for example. In various embodiments, necked down portion 36 may comprise an area of first portion 30 that has a shortest distance from side to side in the widthwise wise direction, e.g., a smallest diameter section. Additionally, shank portion 39 may include a plurality of scallops 33 (indentations and/or oblong indentations) adjacent the distal end 30D, for example. In the example embodiment, four scallops 33 are symmetrically disposed at the distal end 30D of first portion 30 and the distal end 30D flares back out from necked down portion 36, e.g., distal end 30D comprises a larger diameter section than necked down portion 36 (when viewed in cross-section). In other embodiments, the distal end 30D of first portion 30 may include a rectangular geometry.

Figure 4:
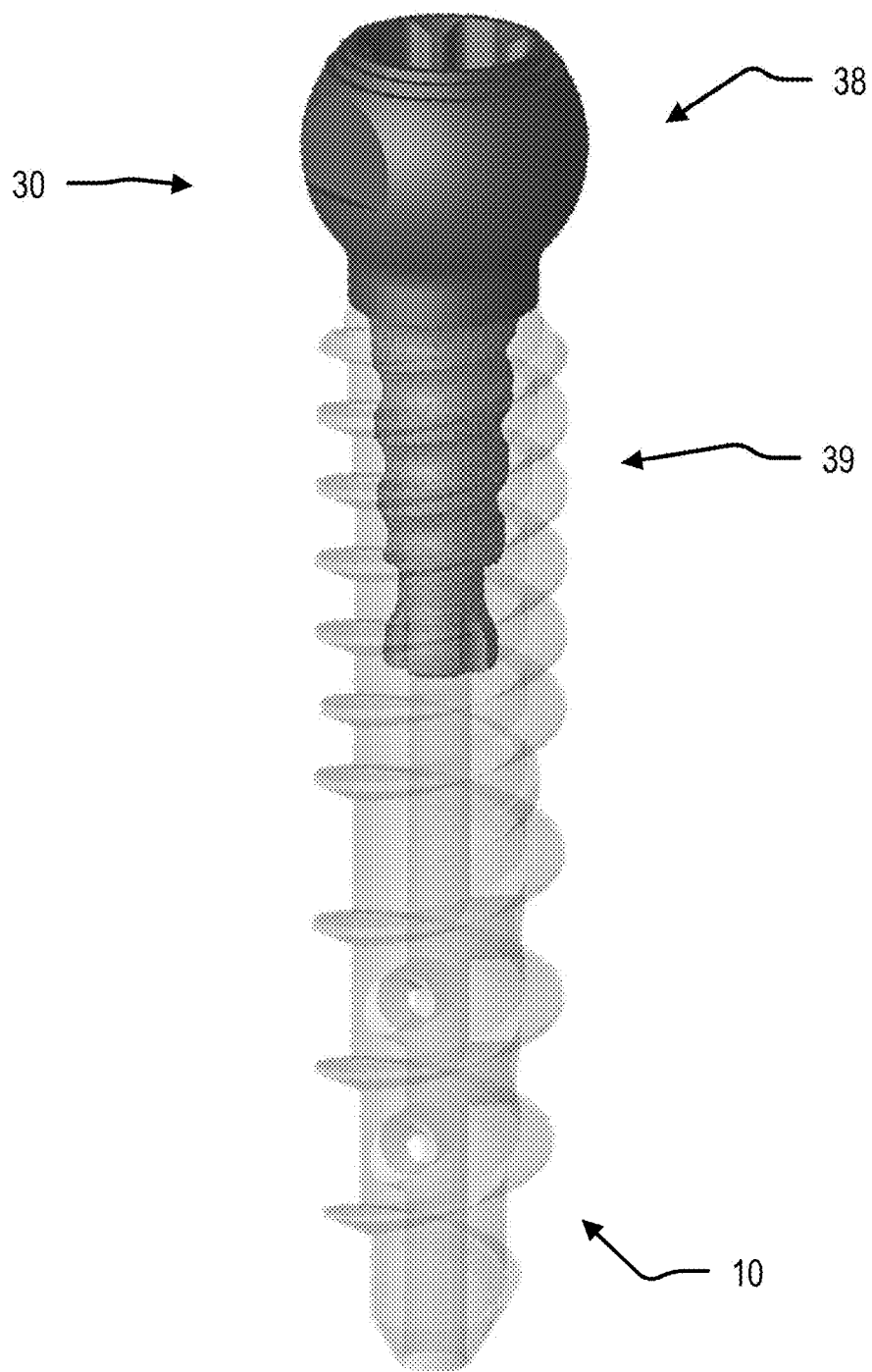
FIG. 4 is a transparent view of a bone screw including a head portion, shank portion, and an overmold.

FIG. 4 is a transparent view of a bone screw 100 including a first portion 30 comprising the upper portion 38 and a second portion 10 comprising an overmold, for example. In various embodiments, the first portion 30 may comprise a metallic material, be formed substantially of a metallic material, and/or be formed purely of a metallic material, e.g., titanium, titanium alloys, etc. However, it shall be understood that other biocompatible materials having similar material properties may also be used. In various embodiments, the second portion 10 may comprise a thermoplastic material, be formed substantially of a thermoplastic material, and/or be formed purely of a thermoplastic material, e.g., PEEK and PEEK composites. However, it shall be understood that other biocompatible materials having similar material properties may also be used.

Example embodiments in accordance with the principles of this disclosure may be formed by an overmold manufacturing process, for example. In various embodiments, first portion 30 may serve as a substrate for which second portion 10 may be overmolded on top of. For example, in various embodiments the first portion 30 serves as a substrate material or part that may be placed into an injection molding tool and/or injection mold and then the overmold material may be injected into, onto, and/or around the first portion 30 which serves as a substrate. The overmold material may be melted in a fluid form and include any relevant biocompatible material, such as PEEK, as explained previously. Thereafter, the overmold material may cure or solidify around the first portion 30 thereby taking the particular shape of the injection mold and securely coupling to the substrate. After the overmold material cures or solidifies, the two materials become joined together as a single part, e.g., bone screw 100. In the example embodiment, the first portion 30 and the second portion 10 are mechanically interlocked together due to the various geometrical contouring of first portion 30, e.g, threads 32, necked down portion 36, scallops 33, and widened distal end 30D function in coordination to transfer rotational forces and axial separation forces between the two different materials of first portion 30 and second portion 10 such that they do not become separated during ordinary usage.

Figure 5:
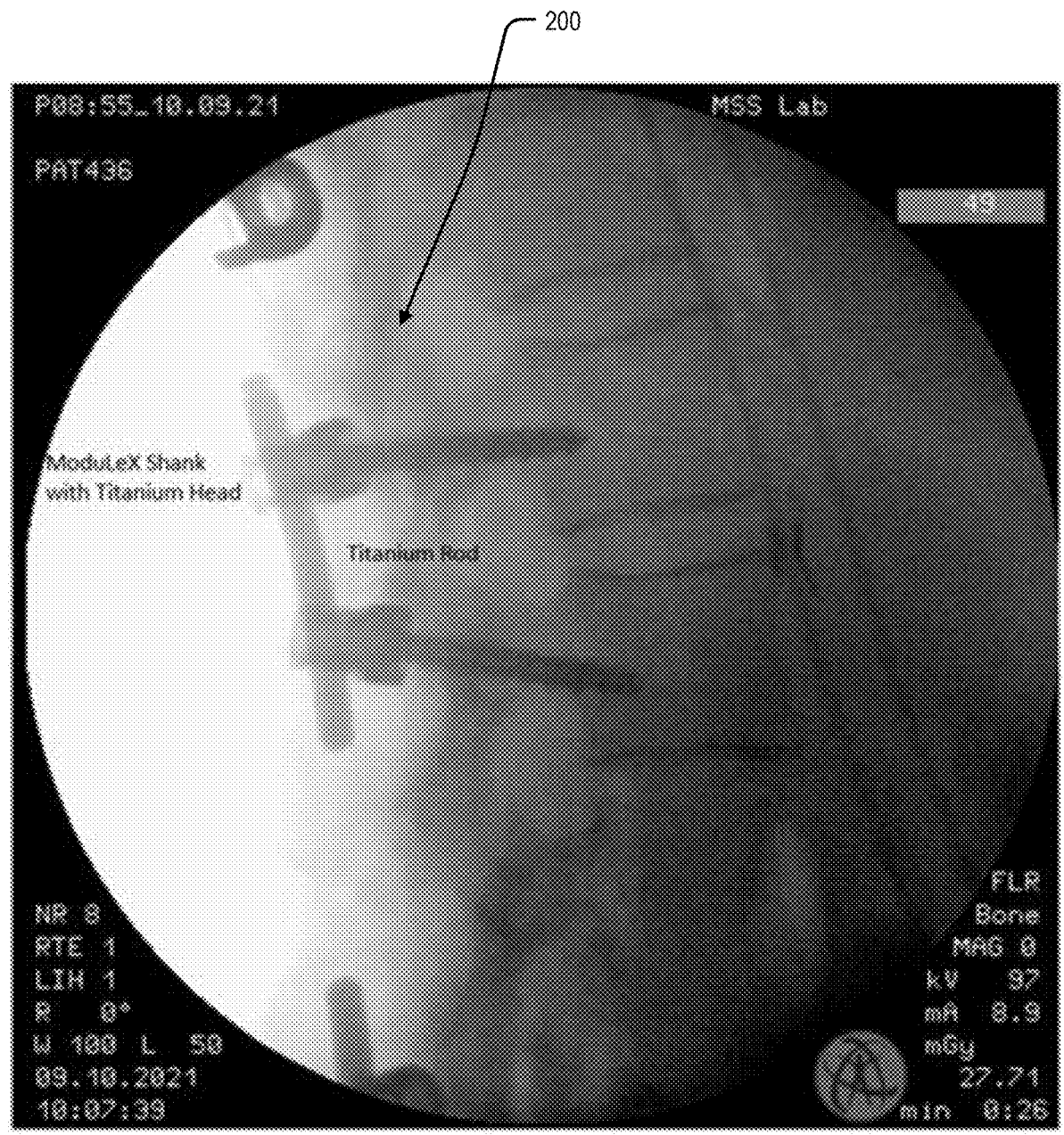
FIG. 5 is an X-Ray image of an entirely metallic spinal support system including a bone screw, receiver, and rod.
Figure 6:
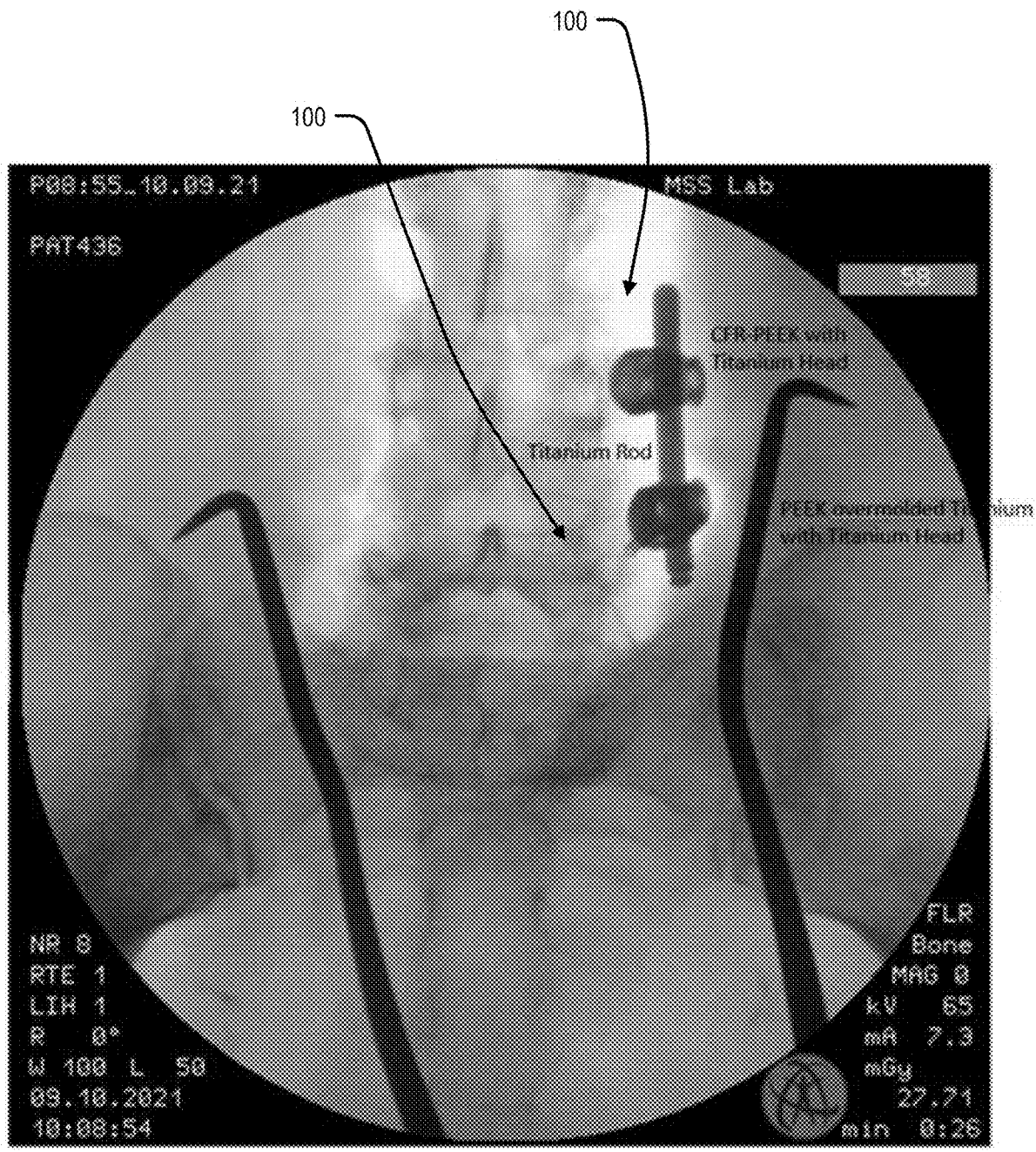
FIG. 6 is an X-Ray image of a first bone screw including both metallic and non-metallic materials.
Figure 7:
FIG. 7 is an X-Ray image of a bone screw including both metallic and non-metallic materials.

Referring generally to FIGS. 5-7, experimental testing of embodiments in accordance with the principles of this disclosure will be discussed. FIG. 5 is an X-Ray image of an entirely metallic spinal support system 200 including a bone screw, receiver, and rod In the example illustration, it is shown that the metallic material is highly visible on the contrasting X-ray image. FIG. 6 is front view of an X-Ray image of a first bone screw 100 (top screw) form completely of continuous fiber reinforced thermoplastic. Additionally FIG. 6 illustrates a second bone screw 100 (bottom screw) formed of a titanium first portion 30 and a second portion 10 formed as a PEEK overmold by an overholding process as explained above. FIG. 7 is a side view of FIG. 6. As seen by the various X-Ray images of FIGS. 5-7, bone screw 100 embodiments including a metallic first portion are visible by X-Ray, but are not nearly as highly contrasting as bone screws 200 formed of entirely metallic materials. Additionally, bone screw 100 embodiments (bottom screw) are capable of showing a trajectory of the bone screw 100 because the first portion 30 includes an elongated shank portion extending in a direction along the longitudinal axis of the bone screw 100. Accordingly, the different material choices have distinct advantages in the context of X-ray imaging because the total mass of metallic material may be reduced, thereby also reducing interference or obfuscating viewing angles of X-Ray imaging. Bone screws 100 may be particularly advantageous when taking X-ray images of tumor patients or those patients with weakened boney anatomy where a surgeon may require high quality X-ray imaging to perform a procedure, verify a procedure, and/or assess future procedures, for example.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A bone screw, comprising:
    a single elongate part extending in a longitudinal direction from a proximal end to a distal end of the bone screw;
    wherein the proximal end comprises a first portion having a head portion coupled to a shank portion,
        the first portion comprising a metallic material, and
        the shank portion comprising a threaded area, a scalloped area that has a first diameter, and a necked down area that is (i) positioned between the threaded area and the scalloped area and (ii) has a second diameter less than the first diameter; and
    wherein the distal end comprises a second portion mechanically interlocked with the first portion via the threaded area, the scalloped area and the neck down area of the shank portion,
        the second portion surrounding the shank area of the first portion and having an exposed thread pattern and an exposed leading tip, and
        the second portion comprising a thermoplastic material.

2. The bone screw of claim 1, wherein:
    the first portion consists essentially of metallic material, and
    the second portion consists essentially of thermoplastic material.

3. The bone screw of claim 1, wherein the first diameter of the scalloped area increases in the longitudinal direction towards the distal end of the bone screw.

4. The bone screw of claim 1, wherein the scalloped area comprises a plurality of scallops symmetrically disposed around the distal end of the bone screw.

5. The bone screw of claim 1, wherein the single elongate part comprises an overmolded part in which the shank portion serves as a substrate on top of which the second portion is molded.

6. The bone screw of claim 1, wherein:
    the first portion consists essentially of titanium, and
    the second portion consists essentially of PEEK.

7. The bone screw of claim 1, wherein:
    the first portion consists essentially of titanium, and
    the second portion consists essentially of a continuous fiber reinforced thermoplastic.

8. The bone screw of claim 1, wherein:
    the threaded area of the shank portion includes a helical thread pattern and an interior of the second portion includes a corresponding helical thread pattern which facilitates a mechanical interlocking of the first portion to the second portion.

9. The bone screw of claim 1, wherein the leading tip comprises a metallic material.

10. A spinal implant system, comprising:
    a bone screw including a single elongate part extending in a longitudinal direction from a proximal end to a distal end, wherein:
        the proximal end comprises a first portion having a head portion coupled to a shank portion,
            the first portion comprising a metallic material, and
            the shank portion comprising a threaded area, a scalloped area with a first diameter, and a necked down area that is (i) positioned between the threaded area and the scalloped area and (ii) has a second diameter less than the first diameter; and the distal end comprises a second portion mechanically interlocked with the first portion via the threaded area, the scalloped area and the neck down area of the shank portion, the second portion surrounding the shank area of the first potion and having an exposed thread pattern and an exposed leading tip, and the second portion comprising a thermoplastic material; and a receiver having a rod receiving passageway extending through a first sidewall and through a second sidewall of the implant receiver, the receiver having a threaded passageway configured to receive a set screw for securing a rod within the rod receiving passageway, the receiver comprising a base portion and at least one locking ring;

wherein, in a locked position, the head portion of the bone screw is securely coupled to the receiver via the base portion and the at least one locking ring.

11. The bone screw of claim 10, wherein:

the first portion consists essentially of metallic material, and the second portion consists essentially of thermoplastic material.

* * * * *